United States Patent
Sherman et al.

(10) Patent No.: US 10,159,244 B2
(45) Date of Patent: Dec. 25, 2018

(54) METHOD FOR POOLING HEPATOCYTES

(71) Applicant: LONZA WALKERSVILLE, INC., Walkersville, MD (US)

(72) Inventors: Matthew Sherman, Cary, NC (US); Robert Kaiser, Fuquay Varina, NC (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 104 days.

(21) Appl. No.: 15/054,476

(22) Filed: Feb. 26, 2016

(65) Prior Publication Data

US 2016/0249602 A1  Sep. 1, 2016

Related U.S. Application Data

(60) Provisional application No. 62/121,619, filed on Feb. 27, 2015.

(51) Int. Cl.
*A01N 1/02* (2006.01)

(52) U.S. Cl.
CPC ........... *A01N 1/021* (2013.01); *A01N 1/0278* (2013.01)

(58) Field of Classification Search
CPC ............................. A01N 1/021; A01N 1/0278
See application file for complete search history.

(56) References Cited

U.S. PATENT DOCUMENTS

| 8,569,573 | B2 | 10/2013 | Grompe |
| 2008/0280357 | A1 | 11/2008 | Arseniev |
| 2010/0075294 | A1 | 3/2010 | Dryden |
| 2010/0197015 | A1 | 8/2010 | Reid |
| 2011/0105359 | A1 | 5/2011 | Czerwinski |
| 2013/0062569 | A1 | 3/2013 | Mo |
| 2013/0130374 | A1 | 5/2013 | Powers |

FOREIGN PATENT DOCUMENTS

WO    WO2014045202 A2    3/2014

OTHER PUBLICATIONS

Kluwer Academic Publishers, Investigation of functional and morphological integrity of freshly isolated and cryopreserved human hepatocytes, Cell and Tissue Banking (2000) 1, pp. 55-68.

Yoshihiro Shibata et al, Prediction of hepatic clearance and availability by cryopreserved human hepatocytes: An application of serum incubation method, Drug Metabolism and Disposition (2002) vol. 30, No. 8.

*Primary Examiner* — Satyendra K Singh
(74) *Attorney, Agent, or Firm* — Medler Ferro Woodhouse & Mills PLLC

(57) ABSTRACT

The present invention relates to a novel method for the preparation of a pooled or mixed population of cryopreserved cells (e.g. hepatocytes). In particular, the invention entails the rapid thaw of cells (e.g. hepatocytes), donated from a single individual, which are mixed to create a heterogeneous population and then cryopreserved. The invention also concerns preparations of multi-cryopreserved cells to increase viability prior to immediate use. The process entails reducing exposure to chemical and physical stresses to increase the resultant number of viable cells.

10 Claims, 4 Drawing Sheets

FIG. 1A

| Spin Number | Number of Cells x 10^6 | | Percent Cell Loss | |
|---|---|---|---|---|
| | 30% Percoll | No Percoll | 30% Percoll | No Percoll |
| 0 | 48.8 | 54.6 | 100.0 | 100.0 |
| 1 | 43.5 | 51.4 | 89.1 | 94.1 |
| 2 | 41.4 | 51.5 | 84.8 | 94.3 |
| 3 | 40.7 | 55 | 83.4 | 100.7 |
| 4 | 37 | 52.2 | 75.8 | 95.6 |
| 5 | 35.6 | 53.1 | 73.0 | 97.3 |

LEGEND

Rat hepatocytes were centrifuged sequentially at 30 RCF for 3 minutes with or without a 30% Percoll density gradient. Fig. 1A shows the total number of cells as well as the percent cell loss after each spin. Fig. 1B graphically illustrates the percent cell loss data from Fig. 1A.

METHOD FOR POOLING HEPATOCYTES

CROSS-REFERENCE AND RELATED APPLICATIONS

This application claims the benefit of each of the following applications: U.S. Patent Application No. 62/121,619 filed on Feb. 27, 2015 and which is herein incorporated by reference in entirety.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

FIELD OF THE INVENTION

The present invention relates generally to pooling and cryopreserving hepatocytes from multiple donors.

BACKGROUND

Hepatocytes constitute approximately 80% of the cells in the liver and are critical for both the activation and eventual detoxification of many pharmacological compounds, toxins or xenobiotics. Increased demand for and availability of new drugs, as well as stricter regulatory and safety testing prior to market approval, have made isolated primary hepatocytes an invaluable resource for studying drug metabolism, efficacy and toxicity in a laboratory setting.

In recent years, significant advancements have been made in the isolation and cryopreservation of primary donor hepatocytes, which can be rapidly thawed and immediately used for experimentation. However, studying hepatic metabolism in hepatocytes isolated from one human liver (individual donor) does not accurately reflect liver function in the overall population since variations in gender, age, ethnicity, health status, genetic background, and other factors skew test results. A more accurate measure of hepatic metabolism is to a use a mixture or "pool" of individual donor cells to create a heterogeneous population of hepatocytes.

A number of methods have been proposed for pooling hepatocytes. These protocols often employ lengthy procedures in which cells are exposed to both physical and chemical stress that reduce the total number of viable cells. For example, the method in U.S. Pat. No. 7,604,929 utilizes a density gradient centrifugation step before the second or final cryopreservation step. This subjects the cells to chemical and mechanical stress that either results in cell loss (FIGS. 1A-B) or weakens the cells such that they die during cryopreservation. Another method disclosed in WO 2014/045202 A2 maintains the hepatocytes in a cryopreservative solution throughout the pooling process. Cryopreservative solutions contain toxic reagents, such as dimethyl sulfoxide (DMSO), which are known to cause cell death.

The proposed system and method seeks to employ techniques to reduce cell loss and therefore increase the total number of viable cells throughout the process.

SUMMARY

The application seeks to increase the number of resulting viable cells from a hepatocyte pooling process. One method for cryopreserving hepatocytes from multiple sources comprises the steps of:
A) thawing hepatocytes from a plurality of sources;
B) pooling the hepatocytes from the plurality of sources into a preservation solution;
C) centrifuging the pooled hepatocytes to cause pelleting of both viable and non-viable hepatocytes;
D) removing the preservation solution;
E) combining the viable and non-viable pelleted hepatocytes with a cryopreservative;
F) distributing the pooled hepatocytes into vials; and
G) cryopreserving the hepatocytes in the vials.

The above method can utilize different kinds of hepatocytes including those selected from the group comprising: human hepatocytes, porcine hepatocytes, simian hepatocytes, canine hepatocytes, feline hepatocytes, bovine hepatocytes, equine hepatocytes, ovine hepatocytes and rodent hepatocytes.

The individual sources can be pooled based on gender, race, age, metabolic state or health state. In some instances, the pools can be randomized based on the sample set that exists at the time.

The kinds of preservation solution that can be used include: University of Wisconsin solution, HYPOTHERMOSOL® BASE (BioLife Solutions, Bothell, Wash.), or HYPOTHERMOSOL-FRS® (BioLife Solutions, Bothell, Wash.) as well as other similar preservation solutions that reduce the toxicity of the cryopreservative and/or provide essential nutrients for the hepatocytes. For example, the preservation solution could include fetal bovine serum.

The centrifugation step is devoid of a density gradient to reduce physical and chemical stress on the cells. This centrifugation step pellets both viable and non-viable hepatocytes.

The pellets can be combined with a cryopreservative prior to being frozen. When combining the cryopreservative and the pelleted cells, pipetting up and down, vortexing, rocking the vial back and forth, tapping the vial or similar processes can be used to resuspend the cells in the cryopreservative solution.

When distributing the pelleted hepatocytes into vials via aliquoting or other methods, the pooled cells can be distributed at a density that ranges from 8-15 million cells/ml. In one embodiment, 13.33 million cells/ml is used.

After the final thaw of the pooled hepatocytes, a user can perform density gradient fractionation to separate viable and non-viable cells immediately prior to performing experiments. In some instances, the density gradient centrifuging step is performed between 50-200 RCF. The density gradient fractionation can comprise density gradient centrifugation through polyvinylpyrrolidone-coated colloidal silica particles (PERCOLL®, Sigma-Aldrich).

The hepatocytes used in these processes can either be plated or used in suspension.

BRIEF DESCRIPTION OF THE DRAWINGS

FIGS. 1A-B illustrate the yield of viable rat hepatocytes after sequential centrifugation with or without a PERCOLL® gradient.

DETAILED DESCRIPTION

Figure 1B:
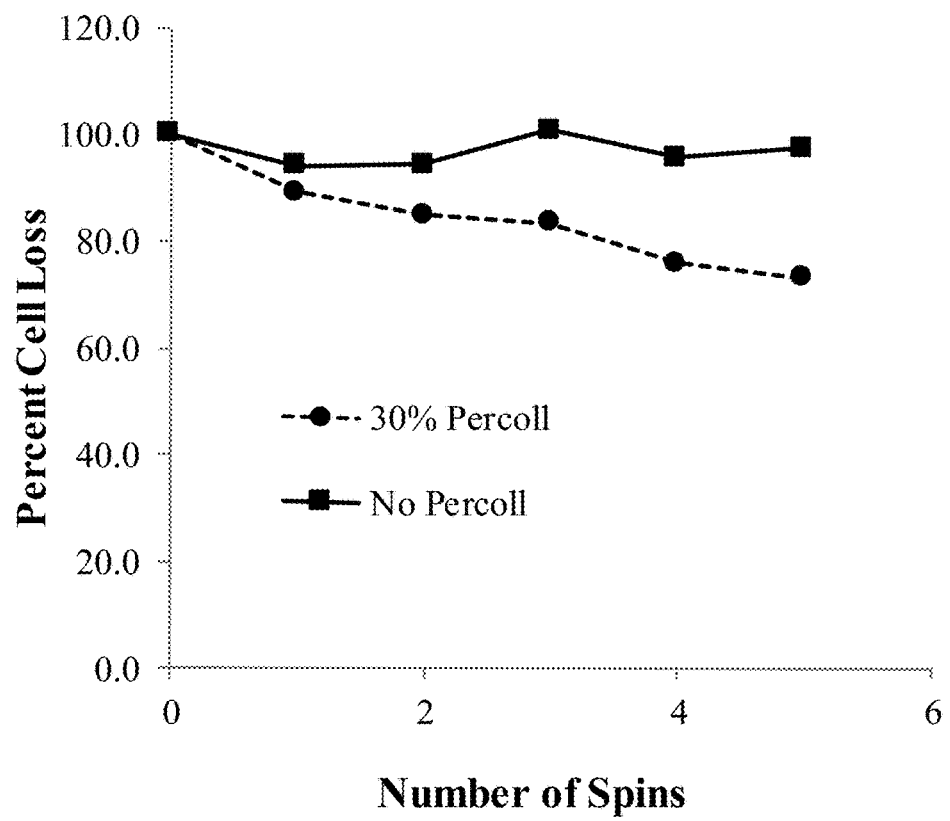

A description of an improved system and method for preparing a cryopreserved pool of cells (e.g. hepatocytes) from previously cryopreserved hepatocytes obtained from individual donors is described herein. This system and method reduces physical and chemical stress to the hepatocytes during the pooling process while increasing the recovery of viable pooled cells during a post-thaw centrifugation step performed by the end-user. In general, this system and method involves thawing vials of individual donor hepatocytes and pooling them into a preservation solution. The pooled cells are then briefly centrifuged, to pellet both viable and non-viable cells, and then cryopreserved at a high density in multiple vials. The end-user can then perform density gradient centrifugation to separate viable from non-viable cells immediately prior to experimental use. Some of the advantages of the proposed method are decreasing the exposure to mechanical, chemical and other environmental factors that reduce the number of viable cells prior to experimenting on the pooled hepatocytes.

In one embodiment, previously isolated and cryopreserved hepatocytes from individual donors are stored in liquid nitrogen vapor phase at a minimum of −150° C. Individual donor vials to be pooled can be selected at random or based on specific metabolic activity (e.g. ECOD, cytochrome P450, general phase I or phase II), age, race, sex, ethnicity, or other phenotypic determinants. The number of vials thawed depends on the number of individuals included in the mixed population and the size of the pool to be generated. For example, the number of individual vials used for each pool of hepatocytes can be from 2-50 individuals. Each pool can range from 300 to 1000 vials. For example, a 10 donor pool with 300 vials would require approximately 30 vials from each donor.

The individual donor hepatocytes are thawed by submerging the vial in a water bath maintained at 37° C. for approximately 2 minutes or until a spindle of ice is barely visible and then the contents are rapidly decanted into a vessel containing a preservation solution at 4° C. The preservation solution is used to dilute the DMSO (and/or any other reagents toxic to the hepatocytes) found in the cryopreservative. In some instances, the preservation solution also provides essential nutrients to the hepatocytes to promote viability during the pooling process. The volume of the preservation solution is dependent on the size of the pool to be generated but can be composed of, for example, a 1:1 ratio of preservation solution to 1 mL of cryopreserved cells. The preservation solution can be composed of University of Wisconsin solution (10 mM potassium lactobionate, 25 mM KH2PO4, 5 mM MgSO4, 30 mM Raffinose, 5 mM Adenosine, 3 mM Glutathione, 1 mM Allopurinol, and 50 g/L Hyroxyethyl starch), HYPOTHERMOSOL® BASE (HTS-Base), HYPOTHERMOSOL-FRS® (HTS-FRS), or other such medium with or without the addition of fetal bovine serum (FBS). The hepatocytes are maintained in the preservation solution at 4° C. while multiple vials of hepatocytes are thawed and mixed in the same vessel to create a "pooled" population of multiple donor cells. Thawed hepatocytes can remain in preservation solution from 2-10 hours depending on the number of vials being thawed.

After multiple vials of hepatocytes have been thawed and pooled, the cells are centrifuged in a range of 50-200 relative centrifugal force (RCF) for 8-10 min to pellet both viable and non-viable cells. The preservation solution is removed from the pelleted cells for example by aspiration. Using a centrifugation step without a density gradient at this point in the process, reduces the physical and chemical stress on the hepatocytes before the second cryopreservation. FIGS. 1A-B illustrate the affect that density gradient (e.g. PERCOLL®) centrifugation can have on hepatocytes compared to centrifugation without a density gradient. With each subsequent spin, the total number of viable cells was reduced with the density gradient (PERCOLL®) relative to hepatocytes centrifuged without PERCOLL®. These results indicate that centrifugation with a density gradient solution reduces the total number of viable cells.

After the cells are pelleted and the preservation solution removed, they are immediately resuspended in a crypotectant solution which can, for example, be composed of CryoStor® CS10 containing DMSO at 10%. The pooled non-viable and viable hepatocytes are then distributed at 10-15 million cells/mL in 1-1.5 mL aliquots per vial. It should be noted that cell counting can be performed without or with for example Trypan blue, Acridine orange, or propidium iodide along any of the steps in the process.

The combining or resuspending process can be comprised of adding a cryopreservative to the pelleted hepatocytes. The combined pellets and cryopreservative can then be pipetted up and down, vortexed, rocked in a vial back and forth, tapped in a vial or some other similar process to break up the pellets and disperse the hepatocytes throughout the cryopreservative.

Vials containing pooled hepatocytes are frozen using a controlled rate freezer and maintained in liquid nitrogen at a minimum of −150° C. for at least 3 days and no longer than 10 years prior to shipping. The vials can be shipped on dry-ice or vapor phase liquid nitrogen (e.g. dewar) to the end-user and stored in liquid nitrogen at a minimum of −150° C. Immediately prior to use, the end-user can thaw the pooled hepatocytes by submerging the vial in a water bath maintained at 37° C. for approximately 2 minutes or until a spindle of ice is barely visible.

The pooled non-viable and viable hepatocytes cells can be applied to a 20-30% colloidal silica coated with polyvinylpyrrolidone (PERCOLL®) gradient, and centrifuged through at 50-200 RCF for 8-10 min to separate viable from non-viable cells. The maximum number of viable cells are therefore isolated immediately prior to use without further exposure to cryopreservative or another freeze-thaw cycle. This process allows for 5 million and up to 8+ million viable cells that can be recovered and immediately used for experimentation. Experimentation may include but not be limited to assays for viability; metabolic activity; transporter activity; and xenobiotic uptake, metabolism, efficacy, and toxicity.

Figure 2:
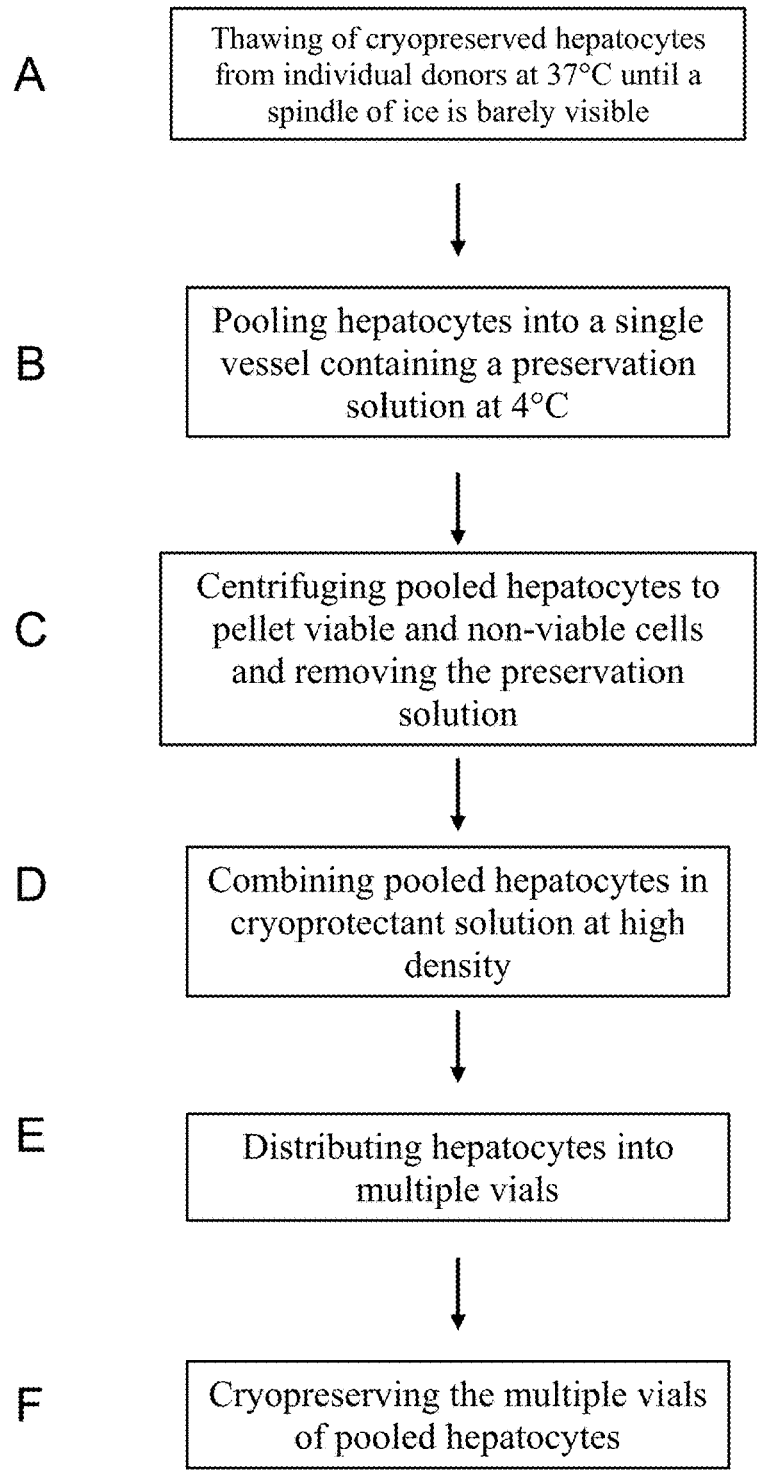
FIG. 2 is a schematic of a method for pooling and cryopreserving hepatocytes from previously cryopreserved hepatocytes from individual donors.
Figure 3:
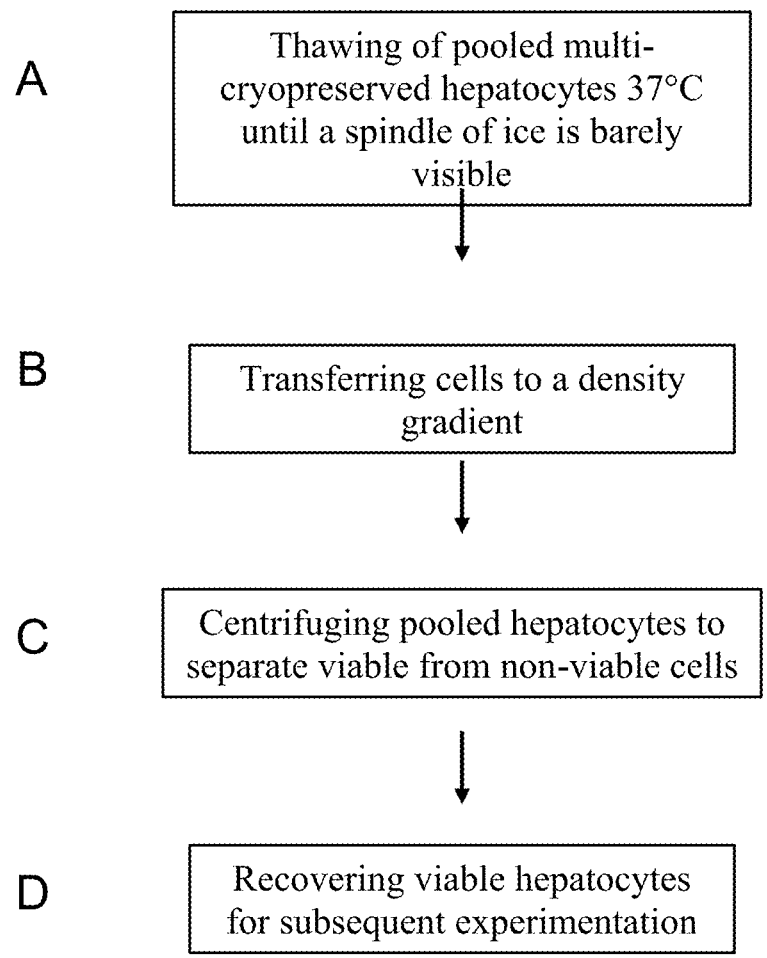
FIG. 3 is a schematic of a method to separate viable from non-viable cells from the last cryopreservation step of FIG. 2.

Procedure for the preparation of pooled hepatocytes from individual cryopreserved donor hepatocytes are shown in FIG. 2 and set forth in the following operation:

1-A. Vials of cryopreserved hepatocytes from 10 individual donors are thawed for approximately 2 minutes in a 37° C. water bath until a spindle of ice is barely visible. It should be noted, some pools can be composed of between 500 and 900 vials, or in this example 50 to 90 vials per donor.

1-B. The thawed hepatocyte suspension (1 mL) is pipetted into a 1 L beaker containing 500 mL of HYPOTHERMOSOL-FRS® preservation solution and maintained at 4° C. to generate a hepatocyte pool.

1-C. The pooled hepatocytes are centrifuged at 100 G for 10 minutes out of the preservative solution (FRS) to pellet both viable and non-viable cells.

1-D. The preservation solution is removed by aspiration and the cells are gently resuspended (e.g. rocked back and forth) in the cryoprotectant CRYOSTOR® CS10 medium. Cells are counted using Trypan blue exclusion to determine cells density and additional cryoprotectant solution is added, if needed, to achieve approximately 13.3×10^6 cells per mL.

1-E. 1.5 milliliters or approximately 20 million cells are aliquoted into individual vials.

1-F. The vials of pooled hepatocytes are cryopreserved in a controlled rate freezer and stored in liquid nitrogen vapor phase at a minimum of −150° C.

Procedure for the separation of viable cells from pooled hepatocytes as performed by the end-user are show in FIG. 2 and set forth in the following operation:

2-A. A vial of pooled hepatocytes is thawed for approximately 2 minutes in a 37° C. water bath until a spindle of ice is barely visible.

2-B. The hepatocyte suspension is carefully applied to a 20-30% PERCOLL® density gradient.

2-C. The samples are centrifuged at 200 RCF for 10 min to separate viable and non-viable cells.

2-D. A minimum of 5 million viable cells are recovered and used immediately for experimentation.

It should be noted that yield of viable cells can vary with dilution ratios, and exposure of time during the pooling process. For example, in larger batches it is sometimes cost prohibitive or difficult (volume of pooling container) to have a 1:1 ratio of preservation solution to thawed cryopreservative. In addition, more time is required to thaw a large number of vials. Thus the cells are exposed to increased concentrations of cryopreservative toxins for a longer period of time. It is sometimes easier to do smaller batches, in which the cryopreservative is more dilute and pooling time is reduced, which generally results in higher yields of viable hepatocytes. For example, step 2-D might yield 5 million viable cells for a larger batch, but up to and greater than 8 million viable cells in a smaller batch. In smaller batches the ratio may be 4:1 preservation solution to thawed cryopreservative.

The processes herein can be applied to hepatocytes used in suspension or plated.

Though the examples describe hepatocytes the method and processes could be applied to other cell types.

These embodiments and features illustrated and described herein are exemplary but not intended to be limiting nor are the claims listed at the end of this application. Multiple combinations and equivalent component parts, ranges and steps are considered within the scope of this application.

What is claimed is:

1. A method for cryopreserving hepatocytes from multiple sources comprising the steps of:
   A) thawing hepatocytes from a plurality of sources;
   B) pooling the hepatocytes from the plurality of sources into a preservation solution;
   C) centrifuging the pooled hepatocytes to cause pelleting of both viable and non-viable hepatocytes, wherein the centrifugation step is devoid of a density gradient;
   D) removing the preservation solution;
   E) combining the viable and non-viable pelleted hepatocytes with a cryopreservative to form pooled pelleted hepatocytes;
   F) distributing the pooled pelleted hepatocytes into vials; and
   G) cryopreserving the pooled pelleted hepatocytes in the vials to form pooled cryopreserved hepatocytes.

2. The method of claim 1, wherein said hepatocytes are selected from the group consisting of human hepatocytes, porcine hepatocytes, simian hepatocytes, canine hepatocytes, feline hepatocytes, bovine hepatocytes, equine hepatocytes, ovine hepatocytes and rodent hepatocytes.

3. The method of claim 1, wherein said multiple sources are comprised of a random or pre-selected group based on gender, race, age, metabolic state or health state.

4. The method of claim 1, wherein the preservation solution is comprised of University of Wisconsin solution.

5. The method of claim 4, wherein the preservation solution is further comprised of fetal bovine serum.

6. The method of claim 1, wherein distributing the pooled pelleted hepatocytes is done at a density greater than 10 million cells/ml.

7. The method of claim 1, further including thawing the pooled cryopreserved hepatocytes from step (G), and applying a density gradient fractionation process.

8. The method of claim 7, wherein the density gradient fractionation process comprises a density gradient centrifugation performed between 50-200 relative centrifugal force.

9. The method of claim 7, wherein said density gradient fractionation comprises density centrifugation through polyvinylpyrrolidone-coated colloidal silica particles.

10. The method of claim 1, wherein the combining of pelleted hepatocytes with cryopreservative further includes one or more of the following steps: pipetting up and down, vortexing, rocking vial back and forth, or tapping the vial.

* * * * *